United States Patent
Legrand et al.

(10) Patent No.: US 9,447,361 B2
(45) Date of Patent: Sep. 20, 2016

(54) USE OF AT LEAST ONE COPRODUCT FROM THE VEGETABLE OIL REFINING INDUSTRY FOR OBTAINING A PURIFIED TOTAL UNSAPONIFIABLE VEGETABLE OIL PRODUCT

(75) Inventors: Jacques Legrand, Neuilly sur Eure (FR); Alex Saunois, Nogent-le-Roi (FR); Caroline Baudouin, Rambouillet (FR); Philippe Msika, Versailles (FR)

(73) Assignee: LABORATOIRES EXPANSCIENCE, Courbevoie (FR)

( * ) Notice: Subject to any disclaimer, the term of this patent is extended or adjusted under 35 U.S.C. 154(b) by 417 days.

(21) Appl. No.: 13/823,573

(22) PCT Filed: Jan. 31, 2012

(86) PCT No.: PCT/EP2012/051602
§ 371 (c)(1),
(2), (4) Date: May 31, 2013

(87) PCT Pub. No.: WO2012/104319
PCT Pub. Date: Aug. 9, 2012

(65) Prior Publication Data
US 2013/0289009 A1 Oct. 31, 2013

Related U.S. Application Data

(60) Provisional application No. 61/438,023, filed on Jan. 31, 2011.

(30) Foreign Application Priority Data

Jan. 31, 2011 (FR) ...................................... 11 50742

(51) Int. Cl.
*C11B 3/14* (2006.01)
*A61K 8/63* (2006.01)
(Continued)

(52) U.S. Cl.
CPC . *C11B 3/14* (2013.01); *A61K 8/31* (2013.01); *A61K 8/63* (2013.01); *A61K 8/678* (2013.01);
(Continued)

(58) Field of Classification Search
None
See application file for complete search history.

(56) References Cited

U.S. PATENT DOCUMENTS 2,349,270 A * 5/1944 Hickman .............. C07D 311/72
549/413
5,512,691 A 4/1996 Barnicki et al.
(Continued)

FOREIGN PATENT DOCUMENTS

FR 2803598 A1 7/2001
WO WO-2010/004193 A1 1/2010

OTHER PUBLICATIONS

Bruner, G., et al., Spearation of Tocopherols from Deodorizer Condensates by Countercurrent Extraction with Carbon Dioxide, 1991, The Journal of Supercritical Fuids, vol. 4, No. 1, pp. 72-80.*
(Continued)

*Primary Examiner* — Yate K Cutliff
(74) *Attorney, Agent, or Firm* — Foley & Lardner LLP (57) ABSTRACT

The present invention relates to the use of at least one vegetable oil refining industry by-product to obtain a purified total unsaponifiable of vegetable oil cleared of the impurities initially present in the said by-product, advantageously cleared of sapid and odorous compounds and/or chemical compounds resulting from the deterioration and the degradation of vegetable oils. The invention further relates to a method for obtaining a purified total unsaponifiable of vegetable oil from at least one vegetable oil refining industry by-product. The invention further relates to a purified total unsaponifiable of vegetable oil able to be obtained by this method, as well as compositions containing such an unsaponifiable. The invention further relates to such unsaponifiables or such compositions for the use thereof as a drug, medical device, dermatological agent, cosmetic agent or nutraceutical, in humans or animals.

25 Claims, 1 Drawing Sheet

(51) Int. Cl.
    *A61K 8/67*     (2006.01)
    *C07D 311/72*   (2006.01)
    *A61K 8/31*     (2006.01)
    *A61Q 19/06*    (2006.01)
    *A61Q 19/08*    (2006.01)
    *A61K 8/97*     (2006.01)
    *A61K 31/20*    (2006.01)
    *A61K 31/355*   (2006.01)
    *A61K 31/56*    (2006.01)
    *C11B 3/00*     (2006.01)
    *C11C 3/00*     (2006.01)

(52) U.S. Cl.
    CPC .............. *A61K 8/97* (2013.01); *A61K 31/20* (2013.01); *A61K 31/355* (2013.01); *A61K 31/56* (2013.01); *A61Q 19/06* (2013.01); *A61Q 19/08* (2013.01); *C07D 311/72* (2013.01); *C11B 3/00* (2013.01); *C11C 3/003* (2013.01)

(56) References Cited

U.S. PATENT DOCUMENTS 5,702,714 A    12/1997    Goss
2003/0130532 A1    7/2003    Bardet et al.
2004/0030166 A1*   2/2004    Copeland ................ B01D 3/14
                                                              552/545
2005/0250953 A1    11/2005   May et al.
2011/0220483 A1    9/2011    Margnat et al.

OTHER PUBLICATIONS

Fang et al. "Separation of natural tocopherols from soybean oil byproduct with supercritical carbon dioxide," Journal of Supercritical Fluids, Pra Press, US, vol. 40, No. 1, Dec. 2006, pp. 50-58.

Hamilton and Rossel, "Analysis of Oils and Fats," Elsevier Applied Science Publishes, 1986, ISBN 0 85334 383 3, pp. 38-41.

Jiang et al., "Molecular distillation for recovering tocopherol and fatty acid methyl esters from rapeseed oil deodorizer distillate," Biosystems Engineering, Academic Press, UK, vol. 93, No. 4, Apr. 2006, pp. 383-391.

Sarkadi, "Laboratory Deodorizer with a Vaporization Efficiency of Unity," The Journal of the American Oil Chemists' Society, vol. 35, 1958, pp. 472-475.

Schwartz, "Improved Method for Quantitating and Obtaining the Unsaponifiable Matter of Fats and Oils," JAOCS, vol. 65, No. 2, 1998, pp. 246-251.

* cited by examiner

USE OF AT LEAST ONE COPRODUCT FROM THE VEGETABLE OIL REFINING INDUSTRY FOR OBTAINING A PURIFIED TOTAL UNSAPONIFIABLE VEGETABLE OIL PRODUCT

The present invention relates to the use of at least one vegetable oil refining industry by-product to obtain a purified total unsaponifiable of vegetable oil cleared of the impurities initially present in the aforementioned by-product, advantageously cleared of sapid and/or odorous compounds and/or chemical compounds resulting from the deterioration and the degradation of vegetable oils. The invention further relates to a method for obtaining a purified total unsaponifiable of vegetable oil from at least one vegetable oil refining industry by-product. The invention further relates to a purified total unsaponifiable of vegetable oil able to be obtained by this method, as well as to compositions containing such an unsaponifiable. The invention further relates to such unsaponifiables or such compositions for the use thereof as a drug, medical device, dermatological agent, cosmetic agent or nutraceutical, in humans or animals.

The unsaponifiable constitutes the fraction of a fat that, after the prolonged action of an alkaline base, remains insoluble in water and can be extracted by an organic solvent.

Vegetable oils typically contain between 0.5% and 2% unsaponifiables (Schwartz, 1988; Hamilton and Rossel, 1986).

Four large groups or families of substances are present in the majority of vegetable oil unsaponifiables. The largest group generally represents sterols including pentacyclic triterpene alcohols and 4-methylsterols. The second group is generally comprised of tocopherols that can integrate tocotrienols. The two other groups are aliphatic alcohols and saturated and unsaturated hydrocarbons.

The qualitative and quantitative composition of these unsaponifiable fractions varies according to the nature of the vegetable oils from which the unsaponifiables are extracted.

Many biological activities have been attributed to these compounds. They are often used in many applications in the fields of pharmacy, cosmetics and foods.

In particular, sterols are in general used for their cholesterol-lowering, anti-inflammatory or anti-aging properties. Tocopherols, more often called vitamin E and tocotrienols, are natural antioxidants recognised for their antioxidant effects in vivo and in vitro as well as for their vitamin properties. Squalene, principal representative of hydrocarbons, in its natural and hydrogenated form also has particular physicochemical properties which enable it to play a role in pharmaceutical and cosmetic formulations.

Generally, sterols, tocopherols or squalene are fractions of unsaponifiables or a specific constituent of unsaponifiables in the case of squalene—of different physicochemical nature which have been isolated and purified from vegetable oil unsaponifiables.

Various methods have thus been developed to selectively extract these unsaponifiable fractions from vegetable oils. These methods mainly integrate intermediate stages of concentration, fractional crystallisation, precipitation, partition by solvents or molecular distillation, which aim to limit the volumes to be treated in the final step of liquid/liquid extraction of the unsaponifiable. However, in view of the price of raw materials, the steps to be implemented and the volumes to be treated, these methods are not economically viable.

The use of oil refining by-products thus seemed a less costly alternative to produce vegetable oil unsaponifiables.

In particular, deodoriser distillates (DD) represent an oil refining industry by-product particularly rich in unsaponifiables. During the last step of vegetable oil refining, a deodorisation operation is carried out by injection of dry steam in oil maintained under vacuum at high temperature. This is distillation with entrainment by steam of the most volatile components of the oil, notably the compounds responsible for odour and taste, sometimes called the "flavours," free fatty acids and also substances arising from the degradation of oils and/or traces of contaminants.

The vacuum and temperature conditions used during deodorisation, coupled with vapour injection, encourage the entrainment of part of the constituents of the oil unsaponifiable. The by-product represented by the condensate of the vegetable oil stripping steam thus contains a remarkable concentration in unsaponifiable, which justifies its recovery in the unsaponifiable fraction extraction system.

According to the refining conditions selected, and the performances of the industrial equipment and deodoriser distillate condensation and separation systems, highly variable enrichment factors in unsaponifiable, compared to the starting crude oil, can be obtained. They range between 5 and 25.

In the case of soya oil, for example, concentrations of 20%, 20% and 3.5%, respectively, for sterols, tocopherols and squalene can be obtained in DD.

There are thus various extraction methods that isolate and purify tocopherols or sterols from vegetable oil refining industry by-products.

One such example is application FR 2,803,598 of the Applicant which describes a method of selective extraction of specific fractions of unsaponifiables, such as tocopherols (vitamin E) and sterols, by crystallisation or liquid/liquid extraction, using a particular solvent such as chloro-1-butane, from a vegetable oil or a vegetable oil refining industry by-product.

Another example is application WO 2010/004193 which describes a method for extracting by fractionation isolated and purified fractions of unsaponifiable, such as squalene, sterols and vitamin E, from condensates of physical refining and/or vegetable oil deodoriser distillates, notably by distillation and crystallisation. Crystallisation notably makes it possible to isolate and purify sterols and fractional or molecular distillation makes it possible to isolate and purify vitamin E.

Thus, the extraction methods of the prior art make it possible to extract specific purified fractions of vegetable oil unsaponifiables from vegetable oil refining industry by-products, but do not make it possible, because of the physicochemical properties of the various tractions, to extract total purified unsaponifiable, preferentially containing all of the families or constituents naturally present in the unsaponifiable of a given oil.

However, beside the constituents of the unsaponifiable itself, others compounds such as impurities are present in vegetable oil refining industry by-products, such as DD, which do not have desirable activity potential, which denature the product or which have a recognised toxicity factor. Notable examples include:

sapid and/or odorous compounds such as deca-2,4-dienal-(E,E), hexanal, hexanol, 1-hexanol-2-ethyl, terpenes such as β-Caryophyllene, etc.;

chemical compounds resulting from the deterioration and degradation of oils, such as aldehydes, ketones, light hydrocarbons, etc.;

pollutants: traces of phytosanitary residues such as pesticides, etc.;

contaminants that can result from cross contaminations (brassicasterol, etc.).

Thus, the volumes handled at facilities that treat vegetable oils are very large and come from many origins (palm, soya, sunflower, colza, peanut, etc.). The same facilities can thus treat in turn oil of various origins, which necessitates particular attention to the traceability and packaging of the DD manufactured and strict cleaning protocols, but which also creates the risk of cross contamination.

Thus, it is very common to detect in DD, and more particularly in soya DD, a compound such as brassicasterol. Brassicasterol is one of the characteristic constituents of colza oil. Thus, a high content of brassicasterol is cause to suspect with high probability the presence of colza oil. It thus acts as a tracer that can be used to determine the purity of oils and unsaponifiables, notably that of soya, and to identify this pollution.

Because of its systematic presence in trace form as an intermediate in plant metabolism, brassicasterol can be systematically detected in unsaponifiables, but the most recurrent cause of the presence of this compound in unsaponifiables produced from DD is the use of a raw material arising from a mixture of various oils, and notably colza oil.

Standards were set to control the presence of this tracer and to guarantee the purity of prepared products. In particular, the Codex Alimentarius determines the standards and recommendations for food safety, whereas the European Pharmacopeia sets standards for drugs.

For example, both organisations limit to 0.3% of total sterols the relative concentration of brassicasterol in soya oil unsaponifiable.

Whereas all extraction pathways are directed towards the purification of specific families from the viewpoint of their different physicochemical properties, there was a need to develop a new method aimed at obtaining all of the constituents and families of constituents composing the unsaponifiable of a specific vegetable oil from oil refining industry by-products, such as DD, while selectively and substantially eliminating the various impurities present in the aforementioned by-products without qualitatively and quantitatively degrading the various constituents composing the aforementioned unsaponifiable.

The present invention fills this need. The Applicant thus discovered a novel method for obtaining a total unsaponifiable of vegetable oil, of reproducible composition, guarantor of its origin, substantially cleared of the various impurities present in the starting by-products, and in which are preserved the various constituents of the unsaponifiable without being degraded.

The method according to the present invention is thus a method of selective extraction of total unsaponifiable of vegetable oil from a starting product containing many impurities, which was difficult and had not been carried out hitherto, taking into account the fact that the total unsaponifiable consists of a mixture of compounds with highly diverse chemical natures and with highly different physicochemical properties.

Moreover, comparison of the compositions of unsaponifiables of various vegetable oils reveals great variability in the relative concentrations of the principal constituents. It also highlights the presence of specific compounds in relation to particular oils. It was thus not obvious that such a method would be successful in extracting all of the compounds and families of compounds constituting the unsaponifiables of various vegetable oils with a good yield, without degradation, while preserving the composition of the unsaponifiable of each oil of origin.

The Applicant thus discovered an extraction method that responds to all of these requirements, and in particular, that enables the preservation within each large family of unsaponifiables the relative composition of the principal compounds that characterise its oil of origin. The composition of the total unsaponifiable obtained according to the method of the present invention thus makes it possible to determine from which type of vegetable oil the prepared product results.

Finally, the use of a raw material considered as a by-product of the oil refining industry is certainly advantageous in terms of its desirably high content of unsaponifiable as seen above, but such raw material also contains many undesirable, odorous, sapid, unstable and toxic compounds. All these undesirable compounds in refined edible oils that are harmful for health are also undesirable for applications of unsaponifiables in the fields of cosmetics, nutraceuticals or pharmaceuticals.

Classically in the methods of the prior art aimed at purifying vegetable oils, such undesirable compounds can be eliminated from vegetable oils at least partly by a deodorisation step during oil refining. Such a deodorisation step is generally carried out by steam stripping under extreme conditions. Typically, a vacuum on the order of 2 mbar to 4 mbar and a temperature up to 250° C., under a stream of steam, is applied, which leads to a significant loss in unsaponifiable, thus demonstrating the nonselective character of such an operation.

Consequently, the use of an identical method to purify an unsaponifiable by deodorisation, under the same conditions as those used for oils, would not lead to selective purification of the unsaponifiable, would generate significant losses of recoverable compounds and would systematically cause a change in the composition of the unsaponifiable.

Since all the constituents of the mixture to be purified have very similar steam pressures, it appears thus difficult to envisage selective fractionation and elimination of the undesirable compounds under the stabilised vacuum and temperature conditions of deodorisation.

In addition, the steam stripping deodorisation method follows the laws of Raoult and Dalton. From these laws, Sarkadi (J.A.O.C.S. 35, 472-475, 1950) proposed a basic formula to define the impact of various parameters on the efficiency of the method.

$$n_{vap} = \frac{n_{oil}P^o}{EP_v} \ln \frac{C_i^0}{C_l}$$

$n_{vap}$: number of moles of steam
$n_{oil}$: number of moles of oil
$P^0$: total pressure of deodorisation
$P_v$: steam pressure saturating the compound to be eliminated
$C_I^0$ and $C_I$: initial and final concentration of the compound to be eliminated
E: efficiency coefficient It can thus be noted, in view of this formula, that many parameters intervene and interact in deodorisation. From this formula, it thus appears that the operating conditions of separation and elimination of the impurities are very difficult to anticipate, all the more so since the mixture to be treated comprises multiple compounds to be eliminated, for the majority of which steam pressure characteristics and starting concentrations are not precisely known.

In addition, the behavior of the mixture to be treated during the vapor injection phase is directly related to pressure, to temperature and to vapor flow rate which, if incorrectly adjusted, cause the vesicular entrainment, even the runaway, of the distillation during the fractionation phases.

An alternative to deodorisation could be represented by fractional distillation, but this type of hatch chemical engineering operation requires high temperatures and long heating times which are detrimental to the stability of the fragile components of the unsaponifiable, notably tocopherols.

Another alternative could be molecular distillation, but in view of the weak separating power of this technology, molecular distillation provided no particular advantage for solving the problem posed.

In the face of these established facts, one of the principal objectives of the invention was to provide a method to selectively eliminate impurities from total unsaponifiables extracted from oil refining industry by-products.

The Applicant thus discovered a novel method for obtaining total unsaponifiable of vegetable oil that solves this problem and mitigates the disadvantages of the techniques of the prior art, advantageously by the use of stripping operations by a carrier gas under vacuum under conditions that perfectly control a temperature and vacuum gradient in the installation.

In a particularly advantageous way, the method or the use according to the invention includes notably a step of substantial elimination of potentially toxic impurities, namely sapid and/or odorous compounds and/or chemical compounds resulting from the deterioration and the degradation of vegetable oils, by the use of at least one step of stripping by a carrier gas with specific temperature and vacuum gradients, advantageously at a temperature increasing from 80° C. to 250° C. and a progression of 0.5° C./min to 2° C./min and under a vacuum decreasing from 50 mbar to 1 mbar and a progression of 0.1 mbar/min to 10 mbar/min, and even more advantageously at a temperature increasing from 145° C. to 210° C. and a progression of 1° C./min and under a vacuum decreasing from 30 mbar to 2 mbar and a progression of 0.5 mbar/min to 5 mbar/min.

The method according to the invention, notably including one such stripping step, led to the preparation of a total unsaponifiable substantially cleared of any compound presenting a risk of toxicity, such as sapid and/or odorous compounds and/or chemical compounds resulting from the deterioration and the degradation of vegetable oils.

The method according to the invention advantageously comprises the combination of various operations to precisely control the evolution and the transformation of the various specific constituents of the unsaponifiable. The method according to the present invention substantially clears the specific impurities of vegetable oil refining industry by-products, such as DD, and guarantees the quality and the harmlessness of the unsaponifiable obtained.

In addition, the method according to the present invention produces, with a high yield, purified total unsaponifiable which can advantageously be incorporated in cosmetic, dermatological or pharmaceutical compositions, medical devices, or in food compositions, dietary supplements or nutraceuticals, for humans or animals.

The present invention thus relates to the use of at least one vegetable oil refining industry by-product to obtain a purified total unsaponifiable of vegetable oil cleared of the impurities initially present in the aforementioned by-product.

The unsaponifiable of a fat comprises all of the constituents that after basic hydrolysis, such as saponification, are very weakly soluble or insoluble in water and soluble in organic solvents such as ethyl ether, aromatic hydrocarbons and chlorinated solvents, etc.

The unsaponifiable is thus composed of all the non-hydrolysable constituents of the fat as well as those resulting mainly from the saponification of non-glyceride fatty acid esters (sterol esters, waxes, tocopherol esters, etc.). As mentioned above, the four large families that constitute unsaponifiables are sterols, tocopherols, aliphatic alcohols and aliphatic hydrocarbons.

In the context of the present invention, the expression "total unsaponifiable of vegetable oil" means all the constituents and families of constituents naturally present in the unsaponifiable of the oil considered.

The name "total unsaponifiable of vegetable oil" is thus defined by its composition and preparation method. Total unsaponifiable encompasses all the families of constituents naturally present in the unsaponifiable of the oil of origin considered. It is obtained by extraction using an organic solvent as described in the definition above.

In the context of the present invention, total unsaponifiable of vegetable oil is not the result of one or more fractionation or mixing operations aimed at obtaining, in isolated and purified fraction form, a compound or a family of compounds constituting the unsaponifiable. Moreover, the composition of the total unsaponifiable of vegetable oil according to the present invention is equivalent, in terms of relative percentages of the constituents of the various families, to that of the unsaponifiable of the oil of origin.

In the context of the present invention, the expression "purified total unsaponifiable of vegetable oil" means a total unsaponifiable, from which the impurities and toxic products notably present in the starting product have been eliminated, advantageously from which the totality or the quasi-totality of the impurities or toxic products notably present in the starting product have boon eliminated.

In a particularly advantageous way, the purified total unsaponifiable of vegetable oil is obtained by at least one step of extracting the crude total unsaponifiable of vegetable oil from at least one vegetable oil refining industry by-product, typically by saponification and liquid/liquid extraction, followed by a step of purification of the crude total unsaponifiable to remove the impurities described above, preferably by stripping.

In the context of the present invention, the expression "crude total unsaponifiable of vegetable oil" means an unsaponifiable isolated from the vegetable oil refining industry by-product and cleared of all the hydrolysable constituents of the fat, that is to say, cleared of glyceride constituents as fatty acids, mono, di and triglycerides, preferably by saponification followed by extraction with an organic solvent.

In addition, advantageously according to the present invention, the purified total unsaponifiable of vegetable oil is cleared of residual solvents used during the extraction of the unsaponifiable from the oil refining industry by-product.

In particular, the vegetable oil refining industry by-product used in the context of the present invention is a deodoriser distillate (DD) of vegetable oils and/or a physical refining condensate.

In a particularly advantageous way, the purified total unsaponifiable according to the invention is cleared of sapid and/or odorous compounds such as deca-2,4-dienal-(E,E), hexanal, hexanol, 1-hexanol-2-ethyl, terpenes such as β-caryophyllene, etc., and/or chemical compounds resulting from the deterioration and the degradation of vegetable oils, such as aldehydes, ketones, light hydrocarbons and terpenes, etc.

One of the fundamental phenomena of deterioration and degradation of oils is represented by oxidation. The chemical deterioration of unsaturated fats by oxygen in the air begins with the formation of peroxides and then with the formation of scission products. These scission products result from the cleavage of the fatty chain at the double bond(s) which leads to the formation of short-chain compounds such as hydrocarbons, aldehydes and ketones, all volatile, responsible for the rancid odour of oxidised fats. During the fat refining process, these compounds are eliminated during the deodorisation operation and are found concentrated in deodoriser distillates. They are found mainly in the extracted unsaponifiable and must be separated selectively to remove the total unsaponifiable from these noxious compounds.

From their thermal and chemical instability, their odour and their taste, they confer on mixtures that contain them high organoleptic instability, an odour and a taste incompatible with ingestion per os. They also have by their chemical structure an unacceptable toxicity potential in terms of public health and safety.

The multitude of chemical molecules represented by these sapid and/or odorous compounds and/or chemical compounds resulting from the deterioration and the degradation of oils make very difficult their separation from the total unsaponifiable mixture. The Applicant thus discovered in a surprising way that only perfect control of operational parameters, namely vacuum, temperature and vapour injection, enables selective and complete elimination of these compounds without significant loss of the constitutive compounds of the unsaponifiable and without changes in their relative proportions.

Typically according to the present invention, the purified total unsaponifiable contains at most 1000 ppm, advantageously at most 500 ppm, even more advantageously at most 100 ppm, of sapid and/or odorous compounds and/or chemical compounds resulting from the deterioration and the degradation of vegetable oils, compared to the total mass of the unsaponifiable.

Advantageously according to the invention, sapid and/or odorous compounds and/or chemical compounds resulting from the deterioration and the degradation of vegetable oils are eliminated by at least one step of entrainment by carrier gas stripping with a temperature and vacuum gradient, advantageously at a temperature increasing from 80° C. to 250° C., typically from 145° C. to 210° C., and a progression of 0.5° C./min to 2° C./rain, typically of 1° C./min, and under a vacuum decreasing from 50 mbar to 1 mbar, typically from 30 mbar to 2 mbar, and a progression of 0.1 mbar/min to 10 mbar/min, typically of 0.5 mbar/min to 5 mbar/min.

More particularly, the carrier gas stripping step is carried out with a temperature and vacuum gradient, at a temperature increasing from 145° C. to 210° C. and a progression of 1° C./min, and under a vacuum decreasing from 30 mbar to 2 mbar and a progression of 0.5 mbar/min to 5 mbar/min.

In addition, advantageously according to the invention, the purified total unsaponifiable is cleared of phytosanitary product residues, namely pesticides, such as aldrin, dieldrin, alpha, beta and sulfate endosulfans or pirimiphos-methyl, dichlorvos and malathion, advantageously by at least one carrier gas stripping step under vacuum, typically at a temperature between 180° C. and 250° C. and under a vacuum of 1 mbar to 5 mbar.

Phytosanitary products are compounds used on crops and during the storage of seeds; they are also present in a more general way in our environment. They can thus be found concentrated in products extracted from plants. It is advisable to eliminate them to guarantee that manufactured products contain residual levels compatible with the specifications suggested by the various regulations (maximum residue levels, MRL) and to ensure the control of their chemical risks.

In an advantageous way according to the invention, the quasi-totality of pesticide residues present in the starting material (by-product) is eliminated or the residual level in the prepared product (purified total unsaponifiable) is reduced below the quantifiable limit defined for the analytical methods used.

Typically, the level of phytosanitary product residues, such as pesticides, is reduced by at least 95%, advantageously by at least 98%, and even more advantageously by at least 99% in the purified total unsaponifiable, compared to the level in the starting material (oil refining industry by-product).

In a particularly advantageous way according to the invention, the purified total unsaponifiable of vegetable oil is or completely cleared of compounds of the following types: sapid and/or odorous compounds; chemical compounds resulting from the deterioration and the degradation of oils, such as aldehydes, ketones and light hydrocarbons; and traces of phytosanitary residues such as pesticides. In addition, the residual level of contaminants that can result from cross contaminations (brassicasterol, etc.) is advantageously reduced.

Typically, in the context of the present invention, the vegetable oil refining industry by-products arise from the following oils: soya, sunflower, colza, wheat germ, corn germ, olive, palm, palm kernel, cotton, copra, sesame, lupine, coconut, peanut, flax, castor bean, grape seed, squash seed, black currant seed, melon seed, tomato seed, pumpkin seed, almond, hazel nut, walnut, evening primrose, borage, safflower, camelina, oil poppy.

In a particular embodiment according to the present invention, the vegetable oil used in the context of the invention is soya oil or sunflower oil.

In a particularly advantageous way, the vegetable oil used in the context of the invention is soya oil.

The present invention further relates to a method for obtaining a purified total unsaponifiable of vegetable oil from at least one vegetable oil refining industry by-product, wherein the aforementioned purified total unsaponifiable is cleared of the impurities initially present in the aforementioned by-product.

The method of the present invention comprises at least one step of extracting the crude total unsaponifiable of vegetable oil from one or several vegetable oil refining industry by-product(s), typically by saponification and liquid/liquid, and a step of purification of the crude total unsaponifiable to remove the impurities described above, preferably by stripping.

In particular, the method of the present invention comprises the following successive steps:
(1) Saponification in hydroalcoholic medium by a potash-type alkaline base,
(2) Liquid-liquid extraction by an organic solvent of the reaction mixture resulting from saponification diluted beforehand with water,
(3) Washing with water of the organic solution extracted, advantageously by liquid/liquid extraction,
(4) Evaporation of the organic solvent, then (5) Carrier gas stripping under vacuum in order to obtain a purified total unsaponifiable of vegetable oil.

The method of the present invention advantageously comprises a preliminary step of concentrating the unsaponifiable of vegetable oil refining industry by-product, typically by molecular distillation, before saponification step (1).

This is thus preferentially concentration by molecular distillation.

This operation can be integrated into the method to enable preliminary enrichment of the by-products such as deodoriser distillates (DD) weakly titrated in unsaponifiable. This preliminary step is based on the variation in vapour pressure values that exists between the majority fatty acid constituents of DD weakly titrated in unsaponifiable and the constitutive components of the unsaponifiable.

This unitary operation has the aim of obtaining, by distillation, a fraction enriched in unsaponifiable in order to minimise the quantities to saponify and extract during the following operations. By the use of this step, the objective is not to purify the product, but to remove from the DD a concentrated fraction containing the maximum of compounds sought. As a result, the reduction carried out is not critical and its mastery is only justified by the concern of engaging in the downstream phases an intermediate enriched in unsaponifiable.

The specific molecular distillation method, which enables fractionation without continuous heating of the entire medium, is used so as to minimise potential degradations of thermosensitive and oxidisable constituents.

The advantage of using this technology at this stage of the method is to reduce the volumes to be treated in upstream steps by concentrating the raw material and thus reducing the quantities of reagents used, the volumes of solvents used and the volumes of discharges and more generally to increase installation productivity and to lower the cost of the total unsaponifiables of vegetable oils.

According to a particular characteristic of the present invention, the method thus comprises a preliminary step of molecular distillation, preferably at a temperature of roughly 100° C. to 150° C. by maintaining a pressure between $10^{-3}$ mmHg and $10^{-2}$ mmHg, or 0.13 Pa to 1.3 Pa, for example on the order of $10^{-3}$ mmHg. The by-product is typically distilled in a centrifugal or wiped-film molecular device. This molecular distillation step makes it possible to concentrate by a factor of 2 to 20 the unsaponifiable content of the by-products used.

Step (1) of saponification of the DD by-product of the method is carried out in hydroalcoholic medium by a potash-type alkaline base.

Saponification of vegetable fats by an alkaline base is a reaction classically used in the fields of oil refining and soap-making, and even more particularly in the analytical methods aiming at assaying unsaponifiable fats. By the use of this chemical reaction, the goal sought is to arrive at a complete reaction characterised by an absence of residual esters. The means used to reach that goal are systematically the use of a large excess of reagent and a homogeneous reaction medium. The use of an alcohol as reaction solvent eases contact between the reagents and maintains favourable reflux with an optimum reaction time.

Advantageously, the base used is potash or sodium hydroxide. Typically, the hydroalcoholic medium is a mixture of water and short-chain alcohols, mainly methanols or ethanols.

Step (2) of extraction by an organic solvent is advantageously carried out on a liquid/liquid extraction column.

This step extracts the constituents of the unsaponifiable by means of a suitable organic solvent. It is advantageously preceded by an operation of dilution by water of the reaction medium to adjust the alcohol content of the solution and to adapt it to the equilibrium of the system obtained with the organic solvent. Using a liquid/liquid extraction column, injection of the solvent in the opposite direction of the hydroalcoholic solution enables separation of the hydrophilic compounds (soaps, glycerol, etc.) from the hydrophobic compounds (unsaponifiable) by selective solubilisation of the latter in the organic solvent.

Various organic solvents can be used during the liquid-liquid extraction (2) such as alkanes, chlorinated solvents, fluorinated aromatic solvents, tert-butyl ethers, solvents comprising a silicon atom, MeTHF, and mixtures thereof.

In a particular example embodiment according to the present invention, the organic solvent of the liquid/liquid extraction (2) is 1,2-dichloroethane (DCE).

Step (3) of washing with water of the extracted organic solution is a purification step advantageously carried out by liquid/liquid extraction, typically on a liquid/liquid (L/L) extraction column.

Demixing between the two phases in contact during extraction is not total and fine droplets of the hydroalcoholic solution remain in dispersion in the organic solution containing the unsaponifiable in solution. These droplets contain hydrophilic compounds such as soaps, glycerol, alcohol, etc., which it is advisable to eliminate.

Generally performed in continuous mode, the washing operation uses a column that allows the injection of washing water in the opposite direction of the organic phase. The volumetric ratio between the organic phase and the washing water phase is adjusted to obtain maximum efficiency with minimum water consumption. The proportions classically used depend on the type of extraction column used and vary from 0.25 to 4, expressed as the ratio between the volume of washing water and the volume of organic solution to wash.

Step (4) of evaporation of the organic solvent consists in eliminating the organic solvent before proceeding to stripping step (5).

It is carried out on any material classically used to evaporate a solvent and to recover a partially or completely desolvated residue. As an example, a falling film evaporator or a plate evaporator can be used for this operation.

At this stage of the method, the recovered product is not generally completely cleared of organic solvent because the technologies used and the operating conditions (temperature, pressure) do not make it possible to eliminate the totality of the solvent. An additional operation is thus generally necessary to finalise the separation of the solvent and to guarantee a residual solvent level compatible with use in cosmetics, nutraceuticals, pharmaceuticals or medical devices.

It is thus important to eliminate all residual solvents to the degree possible, in order to conform to the specifications of the product, to good manufacturing practice or to other requirements related to quality. The finished products thus cannot contain residual solvent concentrations that exceed safety levels. Certain solvents are indeed known for their toxicity.

Advantageously according to the invention, carrier gas stripping under vacuum (5) comprises a preliminary step (a) of elimination of residual organic solvent, advantageously at a temperature between 80° C. and 145° C. and under a vacuum of 200 mbar to 30 mbar.

In a particularly advantageous way according to the invention, carrier gas stripping under vacuum (5) comprises at least one step (b) of entrainment of sapid and/or odorous compounds and/or chemical compounds resulting from the deterioration and the degradation of vegetable oils, by using a specific temperature and vacuum gradient. Typically, this step (b) is carried out following step (a) mentioned above.

The step (b) of carrier gas stripping under vacuum (5) is advantageously carried out at a temperature increasing from 80° C. to 250° C., typically from 145° C. to 210° C., and a progression of 0.5° C./min to 2° C./min, typically of 1° C./min, and under a vacuum decreasing from 50 mbar to 1 mbar, typically from 30 mbar to 2 mbar, and a progression of 0.1 mbar/min to 10 mbar/min, typically of 0.5 mbar/min to 5 mbar/min, in order to eliminate the sapid and/or odorous compounds and/or chemical compounds resulting from the deterioration and the degradation of vegetable oils.

More particularly, step (b) of carrier gas stripping step (5) is carried out at a temperature increasing from 145° C. to 210° C. and a progression of 1° C./min, and under a vacuum decreasing from 30 mbar to 2 mbar and a progression of 0.5 mbar/min to 5 mbar/min.

An additional objective of this stripping step (5) is thus represented by the systematic elimination of the sapid and/or odorous compounds and/or chemical compounds resulting from the deterioration and the degradation of oils (aldehydes, ketones, light hydrocarbons, etc.) and advantageously traces of phytosanitary residues.

In a particularly advantageous way according to the invention, carrier gas stripping under vacuum (5) further comprises a step (c) of elimination of phytosanitary product residues, such as pesticides, advantageously at a temperature between 180° C. and 250° C. and under a vacuum of 1 mbar to 5 mbar, and even more advantageously at a temperature of 210° C. under a vacuum of 2 mbar. Typically, this step (c) is carried out following step (b) mentioned above.

The last step of vapor stripping according to the invention corresponds to the elimination of phytosanitary product residues such as pesticides.

As seen above, it is advisable to eliminate them to guarantee that manufactured products contain residual levels compatible with the specifications suggested by the various regulations (maximum residue levels, MRL) and to ensure the control of their chemical risks. Step (c) thus advantageously makes it possible to prepare a purified total unsaponifiable of vegetable oil containing at most a level equal to the MRL (maximum residue level) set by the current European directive for pesticides.

It was thus discovered that the gas stripping step according to the invention, by applying particular conditions of temperature, vacuum and dry steam or carrier gas flow rate, enables selective elimination of impurities without loss of the major constituents of the unsaponifiable and without changes in their relative proportions. The particular conditions are obtained by applying a temperature gradient correlated to the vacuum, in other words, by progressing in parallel the temperature and vacuum settings in order to obtain selective distillation of the constituents of the mixture.

This is achieved perfectly by the method according to the invention by judicious programming of temperature and vacuum gradients observing phases of linear progression interspersed with stabilised phases during the stripping step (5).

It is by the definition of a precise phase of the method and continuous control of the vacuum, temperature and carrier gas flow parameters that maximum efficiency of the total elimination of the various constituents can be obtained. Generally, the total elimination of sapid and/or odorous compounds and/or chemical compounds resulting from the deterioration and the degradation of vegetable oils can only be obtained if the totality of the solvent is eliminated, and similarly for pesticides if the two preceding phases were perfectly controlled.

According to a particular characteristic of the invention, the stripping carrier gas (5) is dry steam or a neutral gas such as nitrogen.

In a particularly advantageous way according to the invention, all of the carrier gas stripping under vacuum operations (5), notably stripping steps (a), (b) and (c) are carried out in a single apparatus, while successively varying the various operational parameters that enable progressive and controlled elimination of the impurities present.

This thus led to the reduction of the number of steps of the method and to the improvement of its yield and its productivity.

Performing these various stripping phases in the same apparatus advantageously thus makes it possible to reduce cycle times, to reduce energy needs by a sequence of phases without transfer or cooling and to limit the time maintaining high temperature thus reducing the risks of thermal and oxidative decomposition.

Unexpectedly, the present invention also leads to the lowering of the relative level of contaminants such as brassicasterol which can result from cross contaminations. A significant advantage of this property is to be able to partially correct the impact related to the use of DD raw material and to its inherent risks of cross contaminations between various sources of vegetable oils including the presence of colza oil. In the specific case of total unsaponifiable of soya oil, the method according to the invention, and in particular stripping step (5), notably step (b), advantageously leads to a decrease below the relative level of 0.3% necessary to meet regulatory requirements, in particular when the vegetable oil is soya oil.

The invention also leads in a highly advantageous way to a total unsaponifiable of vegetable oil with all the characteristics of composition of the raw material from which it arises and, more particularly, of the vegetable oil of origin. This property is obtained by the selective elimination of the various impurities without loss of compounds of interest.

The present invention further relates to a purified total unsaponifiable of vegetable oil able to be obtained by the method according to the invention, or directly obtained by the method according to the invention, containing at most 1,000 ppm, advantageously at most 500 ppm, even more advantageously at most 100 ppm, of sapid and/or odorous compounds and/or chemical compounds resulting from the deterioration and the degradation of vegetable oils, compared to the total mass of the unsaponifiable.

Advantageously, such an unsaponifiable has a residual level of phytosanitary products, such as pesticides, of at most 5%, advantageously of at most 2%, and even more advantageously of at most 1%, compared to the level in the starting product, namely the vegetable oil refining industry by-product.

Typically, the residual level of phytosanitary products such as pesticides is thus reduced in the purified total unsaponifiable by at least 95%, advantageously by at least 98%, and even more advantageously by at least 99%, compared to the level in the starting material (oil refining industry by-product).

According to a particular characteristic of the invention, the purified total unsaponifiable of vegetable oil contains at most 100 ppm, advantageously at most 10 ppm, even more advantageously at most 5 ppm, of residual solvent, compared to the total mass of the unsaponifiable.

According to a particular example of the present invention, the purified total unsaponifiable of vegetable oil is a purified total unsaponifiable of soya oil and the aforementioned purified total unsaponifiable of soya oil contains a brassicasterol concentration less than or equal to 0.3% compared to the total mass of sterols of the unsaponifiable.

Typically, the purified total unsaponifiable of vegetable oil is a purified total unsaponifiable of soya oil that contains squalene at a concentration between 0.5% and 15% by mass, advantageously between 1% and 10% by mass, compared to the total mass of the unsaponifiable.

Typically, such a purified total unsaponifiable of soya oil contains tocopherols at a concentration between 10% and 50% by mass, advantageously between 20% and 40% by mass, compared to the total mass of the unsaponifiable.

Advantageously, the aforementioned tocopherols contain alpha-tocopherol at a concentration between 2% and 40% by mass, advantageously between 5% and 20% by mass, compared to the total mass of tocopherols; gamma-tocopherol at a concentration between 40% and 80% by mass, advantageously between 50% and 70% by mass, compared to the total mass of tocopherols; and delta-tocopherol at a concentration between 10% and 50% by mass, advantageously between 15% and 40% by mass, compared to the total mass of tocopherols, in the purified total unsaponifiable of soya oil.

Typically, such a purified total unsaponifiable of soya oil also contains sterols at a concentration between 30% and 70% by mass, advantageously between 35% and 65% by mass, compared to the total mass of unsaponifiable.

Advantageously, the aforementioned sterols contain campesterol at a concentration between 10% and 40% by mass, advantageously between 15% and 30% by mass, compared to the total mass of sterols; stigmasterol at a concentration between 10% and 35% by mass, advantageously between 15% and 25% by mass, compared to the total mass of sterols; and beta-sitosterol at a concentration between 30% and 60% by mass, advantageously between 35% and 50% by mass, compared to the total mass of sterols, in the purified total unsaponifiable of soya oil.

In a particularly advantageous way according to the invention, the purified total unsaponifiable of vegetable oil is a purified total unsaponifiable of soya oil containing squalene, tocopherols, in particular alpha tocopherol, gamma tocopherol and delta tocopherol, as well as sterols, in particular campesterol, stigmasterol and beta-sitosterol, at the concentrations mentioned above.

The present invention further relates to a composition containing a purified total unsaponifiable of vegetable oil, advantageously at a concentration between 0.1% and 98% by mass, even more advantageously from 30% to 70% by mass, compared to the total mass of the composition.

In particular, the composition according to the invention contains a purified total unsaponifiable of soya oil as described above in combination with an unsaponifiable of avocado such as a furanic unsaponifiable of avocado or a sterolic unsaponifiable of avocado, preferably with a furanic unsaponifiable of avocado, advantageously in a ratio of approximately ⅔ for soya and ⅓ for avocado.

Lastly, the present invention further relates to the purified total unsaponifiable of vegetable oil as described above or the composition as described above for the use thereof as a drug, medical device, dermatological agent, cosmetic agent or nutraceutical, in humans or animals, advantageously in the prevention and/or treatment of conjunctive tissue disorders such as osteoarthritis, articular pathologies such as rheumatisms, periodontal diseases such as gingivitis or periodontitis, or in the prevention and/or treatment of disorders of the dermis and/or hypodermis such as cutaneous aging, stretch marks and cellulitis, or disorders of the epidermal barrier such as cutaneous inflammations, skin with atopic tendency, atopic eczema and irritating and/or inflammatory dermatitis.

In particular, the method according to the invention leads to the preparation of a total unsaponifiable of vegetable oil, and in the specific case of a raw material like soya to a product that can be used, in combination with an unsaponifiable of avocado, in the manufacture of drugs for the treatment of osteoarthritis.

From its particular composition related to the presence of all the constituents of the total unsaponifiable of soya oil, such a purified total unsaponifiable of soya oil according to the invention showed biological activity higher than its purified fractions, notably sterols, on the various aspects of metabolism of chondrocytes, fibroblasts and odontoblasts.

In a particular example embodiment, the purified total unsaponifiable of soya vegetable oil can be used in combination with an unsaponifiable of avocado, advantageously in a mixture of furanic unsaponifiable of avocado and unsaponifiable of soya, in a respective ratio of roughly ⅓-⅔.

In addition, in the context of the invention, "medical device" means any instrument, apparatus, equipment, material, product, except for products of human origin, or other item alone or in combination, intended by the manufacturer to be used in humans for medical purposes and whose desired principal action is not obtained by pharmacological or immunological means or by metabolism, but whose function can be assisted by such means.

Creams or other topical products can also be medical devices, as is the case for example for the treatment of atopic dermatitis.

Lastly, the present invention relates to the cosmetic use of a purified total unsaponifiable of vegetable oil as described above or a composition as described above for the prevention and/or treatment of cutaneous disorders of the dermis and/or hypodermis, such as aging, stretch marks and cellulitis or for the prevention and/or treatment of disorders of the epidermal barrier such as skin with atopic tendency and skin with irritating and/or inflammatory dermatitis.

The following examples are given to illustrate the invention:

EXAMPLE 1

Soya Deodoriser Distillate Composition

The market for oils, and more particularly soya oil and DD, is strongly conditioned by the global availability of seeds and by the unceasingly increasing demand for vitamin E and phytosterols for developments related to food, cosmetic or pharmaceutical applications.

This demand encourages the oil industry to optimise deodorisation methods to result in DD that possess a composition highly favourable for the recovery of unsaponifiable fractions.

Modifications made to deodorisation apparatuses mainly aim to increase deodorisation temperature and to install specific condensers to collect deodoriser distillates that are particularly rich in tocopherols and phytosterols.

It is this quality of DD that will be treated preferentially by the novel invention.

As an example, a soya deodoriser distillate composition is given:

| | |
|---|---|
| Sterols and triterpene alcohols | 21% |
| Tocopherols | 18% |
| Squalene | 4% |
| Sapid and odorous compounds | 7% |
| Fatty acids | 23% |
| Glycerides | 27% |

EXAMPLE 2

Distillation of a Soya Deodoriser Distillate

The method of the present invention can advantageously include a pretreatment by molecular distillation in the case of DD with reduced concentration of unsaponifiable. It will be applied to eliminate part of the light fraction of DD, primarily composed of fatty acids, in order to thus obtain enrichment in unsaponifiable of the raw material used in the method.

This test was carried out on a centrifugal molecular device pilot unit, with a maximum capacity of 25 kg/hour. This apparatus is composed of the following elements:

A conical circular rotor, 38 cm diameter,
A water circulation coil (condenser),
Two recovery troughs for residue and distillate,
An induction heating system.

The vacuum unit is composed of a vane pump (primary vacuum) and an oil diffusion pump (molecular vacuum).

The product to be treated is pumped preliminarily toward a continuous degasser, composed of a thin film, falling film evaporator. This pretreatment eliminates, before distillation, potential traces of water (or solvent) and dissolved gas that the raw material might contain. The product thus degassed is then collected by a new pump and then transferred to the distillation chamber (bell under molecular vacuum). Liquid is supplied in the centre of the revolving disc. Thus, under the effect of centrifugal force, the product to be distilled is spread out over the rotor in the form of a thin film. Vapours formed during the distillation process will then be condensed on the walls of the bell and the water circulation coil provided to this end. The distillate obtained, like the heavy fraction running out by an adjacent trough, is collected by a pump and thus recovered.

The parameters used for this operation are as follows:
Supply rate: 16 kg/h
Vacuum: $10^{-2}$ mmHg
Distillation temperature: 110° C.
Distillation rate: 44.5%
Composition of Products:

| Compounds in g per 100 g | Raw material DD | Distillation residue |
|---|---|---|
| Sterols and triterpene alcohols | 22.0 | 36.5 |
| Tocopherols | 10.1 | 17.1 |
| Squalene | 6.1 | 6.9 |
| Sapid and odorous compounds | 21.8 | 6.0 |
| Fatty acids and glycerides | 27 | 31 |

EXAMPLE 3

Distillation of a Sunflower Deodoriser Distillate

This test was carried out on same apparatus as Example 2.

The Parameters Used for this Operation are as Follows:
Supply rate: 18.5 kg/h
Vacuum: $10^{-2}$ mmHg
Distillation temperature: 100° C.
Distillation rate: 82.5%
Composition of Products:

| Compounds in g per 100 g | Raw material DD | Distillation residue |
|---|---|---|
| Sterols and triterpene alcohols | 1.1 | 7.9 |
| Tocopherols | 0.1 | 0.6 |
| Squalene | 0.4 | 1.7 |
| Sapid and odorous compounds | 82 | 53.6 |
| Total unsaponifiable | 7.8 | 18.5 |
| Fatty acids and glycerides | 10.2 | 31 |

EXAMPLE 4

Implementation of the Method on Soya

Raw Material Used:
Soya oil deodoriser distillate
Composition:
Total unsaponifiable content: 35.8%
Sterol content: 20.5%
Tocopherol content: 12.8%
Squalene content: 2.6%
Sapid and odorous compounds content: 3.5%
Relative Sterol Composition
Beta-sitosterol: 42.3%
Campesterol: 21.4%
Stigmasterol: 20.9%
Brassicasterol: 0.2%
Relative Tocopherol Composition
Alpha-tocopherol: 15.3%
Delta-tocopherol: 28.3%
Gamma-tocopherol: 56.4%
Step (1) Saponification:
Into a 50 l reactor equipped with a mechanical anchor stirrer, a double-walled vapour heater and a reflux condenser are successively introduced:
8.84 kg of soya deodoriser distillate
2.7 kg of potash solution
20.6 l of alcohol
The mixture is carried to reflux with stirring for 3 h.
After dilution with water the reaction mixture is transferred to an inert tank with nitrogen which will be used to supply the liquid/liquid extraction column.
Step (2) Extraction:
Column diameter: 60 mm
Solution to extract flow rate→15 l/h
Extraction solvent: 1,2-dichloroethane
Extraction solvent flow rate→18 l/h Step (3) Washing:

Column diameter: 60 mm

Solution to wash flow rate→20 l/h

Water/solution to wash ratio: 1

Water flow rate→20 l/h

Step (4) Purification by Evaporation:

The washed solution is evaporated by treatment on a falling film tubular evaporator heated by vapour at 3 bars.

The solution is supplied at a regular flow rate of 6 l/h and the recirculation temperature is set at 90° C.

When all the solution has been transferred, the temperature is gradually increased to 115° C. and evaporation is stopped as soon as the distilled solvent flow rate is no longer detected.

Step (5) Purification by Stripping Under Vacuum:

The product is then transferred to the stripping reactor and the system is connected.

After the product is loaded in the tank, the temperature is set at 90° C. and then the vacuum is gradually lowered to 50 mbar in 1 hour.

The temperature is then increased to 145° C. in an increment of 1° C./min.

As soon as the temperature is reached and the solvent flow rate is no longer detected at the output of the condenser, dry steam is injected by the sparger at a controlled flow rate to maintain controlled boiling.

After 1 h of injection the temperature is increased to 210° C. in an increment of 1° C./min and at the same time the vacuum is decreased to 2 mbar with a progression of 1 mbar/min.

The distillate, represented by the sapid and/or odorous compounds and/or chemical compounds resulting from the deterioration and the degradation of the oil, is condensed and cooled by the condenser, collected in the collection jar, and then evacuated towards the exterior by a pump.

Vapour supply is then maintained for 5 h at a temperature of 210° C. The product is then cooled under a stream of nitrogen, and then extracted after breaking the vacuum.

The Mass Balance of the Operation is as Follows:

Deodoriser distillate used: 8.84 kg

Sapid and odorous compounds recovered: 0.55 kg

Total unsaponifiable of soya prepared: 2.98 kg

Results:

| | | DD | TU | % recovered |
|---|---|---|---|---|
| Sterol content (GC) | | 18.5% | 53.2% | 96.9 |
| Relative | Brassicasterol | 0.2% | 0.1% | 16.8 |
| Relative | Campesterol | 21.4% | 20.5% | |
| | Stigmasterol | 20.9% | 20.6% | |
| | Beta sitosterol | 42.3% | 42.1% | |
| Total tocopherol content (HPLC) | | 12.8% | 35.4% | 93.1 |
| Relative | Alpha-tocopherol | 15.3% | 15.1% | |
| | Gamma-tocopherol | 56.4% | 61.6% | |
| | Delta-tocopherol | 28.3% | 23.3% | |
| Squalene content | | 2.6% | 4.1% | 53.1 |
| Sapid and odorous compound content | | 3.5% | 0.01% | |

| | DD | TU | % recovered |
|---|---|---|---|
| Pesticide residues (mg/kg) | 103[1] | <QL[2] | <99.5[3] |
| Unsaponifiable content | 35.8%[4] | 33.7%[5] | 94.1[6] |

[1]Sum of alpha-endosulfan, beta-endosulfan and endosulfan sulfate.
[2]Quantifiable limit: 0.5 mg/kg for the sum of the endosulfans.
[3]Percent of pesticide residues eliminated compared to the level in the starting product: (103 − 0.5) * 100/103 = 99.5%.
[4]Unsaponifiable content assayed in the deodoriser distillate.
[5]Unsaponifiable percent yield: mass of purified total unsaponifiable obtained compared to the mass of the deodoriser distillate used.
[6]Extraction percent yield: mass of purified total unsaponifiable obtained compared to the assayed theoretical mass in the deodoriser distillate used.

The composition of the purified total unsaponifiable of soya prepared demonstrates the performance of the claimed method, which:

provides a purified total unsaponifiable of soya oil from a deodoriser distillate of soya, guarantees the presence of the various families of constitutive components of an unsaponifiable of soya, guarantees the preservation of the relative composition of the various families of components, eliminates the sapid and/or odorous compounds and/or chemical compounds resulting from the deterioration and the degradation of vegetable oils, reduces the relative concentration brassicasterol, eliminates traces of pesticide residues, guarantees a high recovery rate of the various components, notably sterols and tocopherols.

EXAMPLE 5

Implementation of the Method on Sunflower

A total unsaponifiable of sunflower is prepared from the distilled raw material in Example 2 using the technology described in Example 4. The particular parameters used are as follows:

Raw Material Used:

Deodoriser distillate of sunflower oil

Composition:

Total unsaponifiable content: 18.5%

Sterol content: 7.9%

Tocopherol content: 0.5%

Squalene content: 1.7%

Sapid and odorous compounds content: 53.6%

Relative Sterol Composition

Beta-sitosterol: 56.9%

Campesterol: 11.1%

Stigmasterol: 12.4%

Delta7-stigmasterol: 5%

Brassicasterol: 0.0%

Relative Tocopherol Composition

Alpha-tocopherol: 87.5%

Reta-tocopherol: 8.8%

Gamma-tocopherol: 3.0%

Step (1) Saponification:

Into a 50 l reactor equipped with a mechanical anchor stirrer, a double-walled vapour heater and a reflux condenser are successively introduced:

18 kg of deodoriser distillate of sunflower concentrated by molecular distillation 9.5 kg of potash solution 40 l of alcohol The mixture is carried to reflux with stirring for 5 h.

After dilution with water the reaction mixture is transferred to an inert tank with nitrogen which will be used to supply the stirred liquid/liquid extraction column.

Step (2) Extraction:
Column diameter: 60 mm
Solution to extract flow rate→15 l/h
Extraction solvent: 1,2-dichloroethane
Extraction solvent flow rate→22.5 l/h Step (3) Washing:
Column diameter: 60 mm
Solution to wash flow rate→15 l/h
Water/solution to wash ratio: 1
Water flow rate→15 l/h Step (4) Purification by Evaporation:
The washed solution is evaporated by treatment on a falling film tubular evaporator heated by vapour at 3 bars.

The solution is supplied at a regular flow rate of 6 l/h and the recirculation temperature is set at 90° C.

When all the solution has been transferred, the temperature is gradually increased to 115° C. and evaporation is stopped as soon as the distilled solvent flow rate is no longer detected.

Step (5) Purification by Stripping Under Vacuum:
The product is then transferred to the stripping reactor and the system is connected.

After the product is loaded in the tank, the temperature is set at 80° C. and then the vacuum is gradually lowered to 50 mbar in 1 hour.

The temperature is then increased to 125° C. in an increment of 0.5° C./min.

As soon as the temperature is reached and the solvent flow rate is no longer detected at the output of the condenser, dry steam is injected by the sparger at a controlled flow rate to maintain controlled boiling.

After 1 h of injection the temperature is increased to 210° C. in an increment of 1° C./min and at the same time the vacuum is decreased to 2 mbar.

The distillate, represented by the sapid and/or odorous compounds and/or chemical compounds resulting from the deterioration and the degradation of the oil, is condensed and cooled by the condenser, collected in the collection jar and then evacuated towards the exterior by a pump.

Vapor supply is then maintained for 5 h at a temperature of 210° C.

The product is then cooled under a stream of nitrogen, and then extracted after breaking the vacuum.

The Mass Balance of the Operation is as Follows:
Deodoriser distillate used: 18 kg
Sapid and odorous compounds recovered: 0.23 kg
Total unsaponifiable of sunflower prepared: 3.08 kg

| | DD | Total unsapon. | % recovered |
|---|---|---|---|
| Sterol content (GC) | 7.9% | 40.1% | 90.4 |
| Relative  Brassicasterol | 0.0% | 0.0% | |
|   Campesterol | 10.6% | 11.7% | |
|   Stigmasterol | 12.0% | 12.9% | |
|   Beta-sitosterol | 55.8% | 57.7% | |
|   Δ7-stigmasterol | 4.8% | 5.1% | |
| Total tocopherols content (HPLC) | 0.6% | 3.0% | 97.1 |
| Relative  Alpha-tocopherol | 87.5% | 87.9% | |
|   Gamma-tocopherol | 3.6% | 5.1% | |
|   Beta-tocopherol | 8.8% | 6.9% | |
| Squalene content | 1.7% | 9.1% | 95.3 |
| Sapid and odorous compound content | 53.6% | 0.01% | |
| Pesticide residues (mg/kg) | 12[1] | <QL[2] | <98.8[3] |
| Unsaponifiable content | 18.5%[4] | 17.8%[5] | 96.2[6] |

[1]Sum of pirimiphos-methyl, dichlorvos and malathion content.
[2]Quantifiable limit: 0.05 mg/kg for each of pesticides, pirimiphos-methyl, dichlorvos and malathion.
[3]Percent of pesticide residues eliminated compared to the level in the starting product: (12 − 0.15) * 100/12 = 98.8%.
[4]Unsaponifiable content assayed in the deodoriser distillate.
[5]Unsaponifiable percent yield: mass of purified total unsaponifiable obtained compared to the mass of the deodoriser distillate used.
[6]Extraction percent yield: mass of purified total unsaponifiable obtained compared to the assayed theoretical mass in the deodoriser distillate used.

Results:
The composition of the purified total unsaponifiable of sunflower prepared demonstrates the performance of the claimed method, which:
provides a purified total unsaponifiable of sunflower oil from a deodoriser distillate of sunflower concentrated beforehand by molecular distillation,
guarantees the presence of the various families of constitutive components of an unsaponifiable of sunflower,
guarantees the preservation of the relative composition of the various families of components,
eliminates the sapid and/or odorous compounds and/or chemical compounds resulting from the deterioration and the degradation of vegetable oils,
eliminates traces of pesticide residues,
guarantees a high recovery rate of the various components, notably sterols and tocopherols.

EXAMPLE 6

Counterexample: the total unsaponifiable extraction from oil with molecular distillation (MD).

Total unsaponifiable of soya was prepared from refined soya oil in two successive steps:

Step 1: Preparation of a fraction concentrated in unsaponifiable by molecular distillation using the technology described in Example 2 with the following operational parameters:
Supply flow rate: 15.5 kg/h
Vacuum: $10^2$ mmHg
Distillation temperature: 230° C.
Distillation rate: 3.9%

Step 2: Extraction of total unsaponifiable by saponification, solvent extraction and deodorisation using the saponification and extraction technology described in Example 4.

Material Balance
Mass of refined soya oil used: 198 kg
Step 1 distillation rate: 3.9%
Total unsaponifiable of soya extracted from the molecular distillation distillate: 7.95%
Total unsaponifiable of soya extracted from the soya oil: 0.31%
Recovery rate: 62%
Composition of the unsaponifiable obtained by MD of the soya oil and extraction:

| | Oil | Total unsapon. | % recovered |
|---|---|---|---|
| Sterol content (GC) | 0.4% | 61.0% | 50.1 |
| Relative  Brassicasterol | 0.3% | 0.3% | |
|   Campesterol | 18.4% | 23.3% | |

-continued

|  | Oil | Total unsapon. | % recovered |
|---|---|---|---|
| Stigmasterol | 15.9% | 20.5% |  |
| Beta-sitosterol | 45.4% | 45.9% |  |
| Total tocopherols content (HPLC) | 0.1% | 27.0% | 70.0 |
| Relative Alpha-tocopherol | 9.8% | 7.3% |  |
| Gamma-tocopherol | 67.7% | 68.8% |  |
| Delta-tocopherol | 22.6% | 23.7% |  |
| Squalene content | 0.01% | 0.6% | 18.5 |
| Unsaponifiable content | 0.50% | 0.3% | 62.0 |

Conclusion:

The composition of the total unsaponifiable of soya prepared demonstrates the following properties of the method of extraction from oil that uses an MD step and an extraction step, which:

provides a total unsaponifiable of soya oil from the oil, guarantees the presence of the various families of constitutive components of an unsaponifiable of soya, guarantees the preservation of the relative composition of the various families of components, does not guarantee a high recovery rate of the various components, notably sterols and squalene.

EXAMPLE 7

Figure 1:
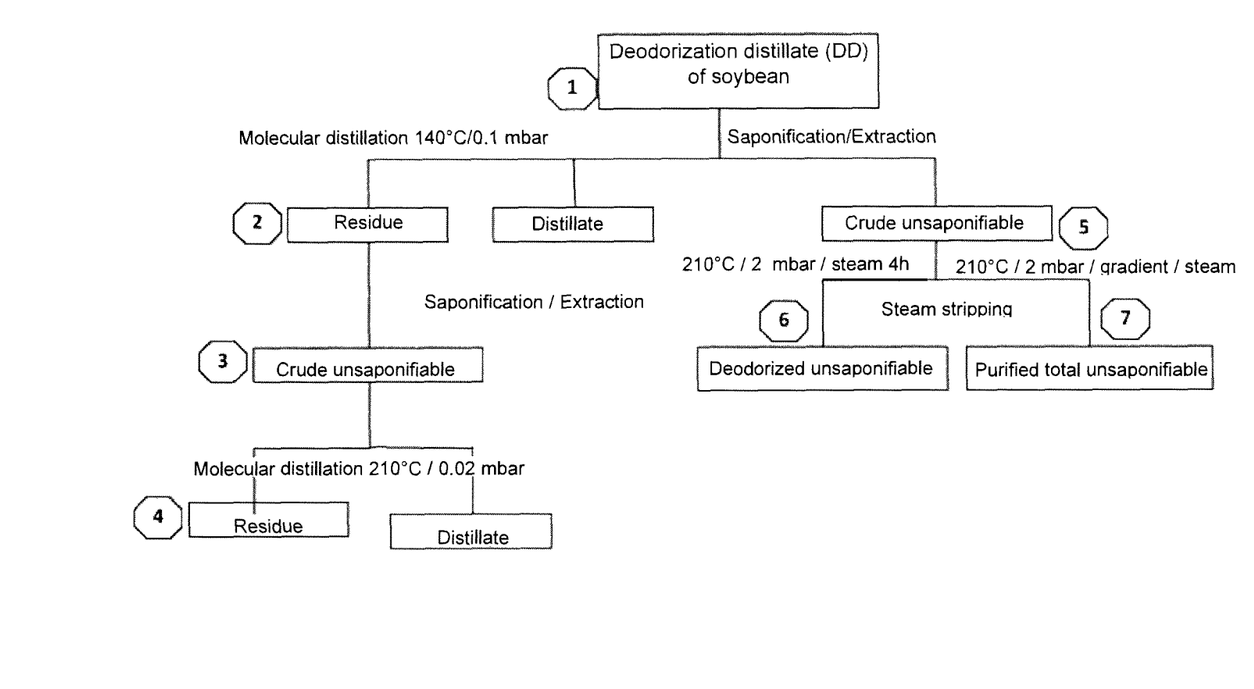

Example Demonstrating the Effectiveness of the Method According to the Invention for the Removal of Pesticides Deodorization techniques and molecular distillation were compared at different stages of the preparation of the soybean insaponifiable from a deodorization distillate of soybean oil according to the present invention. FIG. 1 shows various extraction and purification possibilities of the soybean unsaponifiable.

The left route of FIG. 1 thus presents a molecular distillation step from a deodorization distillate (DD) of soybean oil, leading to a residue 2. The crude total unsaponifiable 3 is then extracted from the residue 2 by saponification/extraction. Molecular distillation at temperature stabilized at 210° C. and 2 mbar was performed on the crude total unsaponifiable 3 to lead to the residue 4.

The right route of FIG. 1 thus presents the obtaining of the crude total unsaponifiable 5 of soybean from a deodorization distillate (DD) of soybean oil 1 by saponification/extraction as described in the example 4 above, in accordance with the present invention. The crude total unsaponifiable 5 is then deodorized one hand to lead to the deodorized unsaponifiable 6 by steam stripping at temperature stabilized at 210° C. and 2 mbar. On the other hand, the purified total unsaponifiable of soybean oil according to the invention is obtained by steam stripping under vacuum, from the crude total unsaponifiable 5, using a gradient of temperature and vacuum specific according to the present invention, using herein the conditions described above in Example 4 in step (5).

The evaluation of pesticide disposal was made on the elimination of aldrin and dieldrin and the results are presented in Table 1 below.

TABLE 1

| Sample | Sample Code (see FIG. 1) | Aldrin mg/kg | Dieldrin mg/kg | Reduction factor Aldrin | Reduction factor Dieldrin |
|---|---|---|---|---|---|
| DD | 1 | 0.41 | 3.40 |  |  |
| DD residue | 2 | 0.20 | 0.72 | 2.05 | 4.7 |
| Crude unsaponifiable | 3 | 0.49 | 2.20 |  |  |
| Unsaponifiable residue after molecular distillation | 4 | 0.1 | 1.00 | 4.9 | 2.2 |
| Crude unsaponifiable | 5 | 0.44 | 6.86 |  |  |
| deodorized unsaponifiable | 6 | Non-detected | 0.30 | >4.4 | 6.7 |
| Purified total unsaponifiable | 7 | Non-detected | Non-detected | >4.4 | >69 |

Non-detected: <LOQ (0.1 mg/kg)

Conclusion

The molecular distillation method applied before or after the step of extraction of the unsaponifiable, shown in the left route of FIG. 1, reduces the residual pesticides content, but does not result in a complete removal.

Deodorisation of unsaponifiable at a stabilized temperature of 210° C. leads to an elimination of dieldrin which is not complete.

However, the steam stripping applied under the conditions described in Example 4 according to the invention leads to a total elimination of dieldrin.

EXAMPLE 8

Biological Activity

Joints are made up of various tissues of which the most important involved in articular pathologies such as osteoarthritis are cartilage, synovial membrane and subchondral bone.

Articular cartilage is conjunctive tissue which, within the joint, is in contact by its deepest layer with subchondral bone and by its surface layer with synovial fluid. The unique properties of cartilage are correlated with the composition and structure of its extracellular matrix, which is mainly composed of a high proportion of proteoglycans such as aggrecan, trapped in a dense network of collagen fibre and a large quantity of water. Joint cartilage comprises cells, chondrocytes, which are responsible for the synthesis and maintenance of the extracellular matrix of the cartilage. In normal cartilage, there is a state of equilibrium established between the synthesis and the breakdown of this extracellular matrix.

With osteoarthritis, cartilage homeostasis is altered via a disturbance of chondrocyte metabolism toward an increase in catabolism and a reduction in anabolism.

One of the principal strategies for anti-osteoarthritis treatments is to inhibit or stop cartilage destruction by:

inhibiting catabolic factors such as inflammation mediators, stimulating cartilage repair mechanisms by increasing the synthesis of major components of the matrix.

The effects of various fractions of unsaponifiables with anti-osteoarthritis potential were evaluated on chondrocyte metabolism of human osteoarthritic cartilage cultivated in alginate beads for 12 days. Various aspects of chondrocyte metabolism were studied in order to draw up the pharmacological profile of these compounds. Their effects were studied on the production of anabolic targets essential to the reconstruction of the cartilage matrix such as aggrecan (AGG) and TGFbeta1 (TGFb1) and catabolic targets involved in cartilage destruction such as interleukin 6 (IL-6) and nitric oxide (NO).

The model of human chondrocyte culture in alginate halls used in this study mimics the environment of chondrocytes in cartilage.

Aggrecan is the majority and specific proteoglycan of hyaline cartilage on which it confers a great resistance to compressions. Moreover, in osteoarthritis, there is a shortage of aggrecan which represents a potential therapeutic target.

Transforming growth factor beta 1 (TGFbeta1) plays a key role in the stimulation and repair of extracellular matrix components. TGFbeta is expressed by chondrocytes and is able to stimulate expression of matrix molecules. Moreover, TGFbeta is also known to exert antagonistic effects on IL-1beta. Thus, to stimulate TGFbeta can have beneficial effects in the prevention of progressive erosion of cartilage that occurs in osteoarthritis.

IL-6 was measured because it is a reference cytokine for evaluating the inflammatory response of cells. In addition, IL-6 decreases the expression of type II collagen and aggrecan in chondrocytes.

Nitric oxide is an activated form of ubiquitous oxygen, involved in the inflammatory response and in oxidative stress. Mediators of oxidative stress play a considerable role in osteoarthritis physiopathology. In particular, nitric oxide is described as contributing to the development of osteoarthritic lesions by limiting cartilage matrix macromolecules on the one hand and by inducing chondrocyte cell death on the other.

The various fractions tested are as follows:
Purified sterolic unsaponifiable fraction of soya: sterol content>95%
Total furanic unsaponifiable fraction of avocado=furanic unsaponifiable fraction of avocado+trihydroxylated alcohol unsaponifiable fraction of avocado+sterolic unsaponifiable fraction of avocado+squalene fraction
Purified total unsaponifiable of soya according to the present invention+total furanic unsaponifiable fraction of avocado The results were expressed in quantity of aggrecan (in ng), TGFbeta1 (in pg), IL-6 (in pg) and $NO_2+NO_3$ (in nmol) per µg of DNA. The mean and reduced standard deviation (SEM) were calculated for each culture condition. The means obtained were compared by the non-parametric Mann-Whitney U test. The percentage of activity of the compounds was calculated compared to the control (cells not treated by the compounds). The results were massed according to statistical significance. Thus: NS=no activity; $p<0.05=+$; $p<0.01=++$; $p<0.001=+++$.

Effect of Fractions on Aggrecan Production

| Conditions | ng AGG per µg DNA | SD | % compared to control | Significance |
|---|---|---|---|---|
| Control | 9804.59 | 601.07 | | |
| Purified total unsaponifiable of soya + total furanic unsaponifiable 0fraction of avocado | 11,568.00 | 522.58 | 118% | p < 0.01 = ++ |
| Total furanic unsaponifiable fraction of avocado + purified sterolic unsaponifiable fraction of soya | 9,517.00 | 1,215.57 | 97% | NS = 0 |

Effect of Fractions on TGFbeta1 Production

| Conditions | pg TGFb1 per µg DNA | SD | % compared to control | Significance |
|---|---|---|---|---|
| Control | 81.47 | 7.35 | | |
| Purified total unsaponifiable of soya + total furanic unsaponifiable fraction of avocado | 106.77 | 9.29 | 131% | p < 0.01 = ++ |
| Total furanic unsaponifiable fraction of avocado + purified sterolic unsaponifiable fraction of soya | 96.59 | 7.07 | 118% | NS = 0 |

Effect of Fractions on IL-6 Production

| Conditions | pg IL-6 per µg DNA | SD | % compared to control | Significance |
|---|---|---|---|---|
| Control | 11,104.73 | 905.06 | | |
| Purified total unsaponifiable of soya + total furanic unsaponifiable fraction of avocado | 7,511.13 | 705.82 | 68% | p < 0.001 = +++ |
| Total furanic unsaponifiable fraction of avocado + purified sterolic unsaponifiable fraction of soya | 9,968.84 | 1,365.94 | 90% | NS = 0 |

Effect of Fractions on NO Production

| Conditions | nmol $NO_2 + NO_3$ per µg DNA | SD | % compared to control | Significance |
|---|---|---|---|---|
| Control | 64.82 | 0.89 | | |
| Purified total unsaponifiable of soya + total furanic | 54.74 | 0.91 | 84% | p < 0.01 = ++ |

| Conditions | nmol NO₂ + NO₃ per μg DNA | SD | % compared to control | Significance |
|---|---|---|---|---|
| unsaponifiable fraction of avocado Total furanic unsaponifiable fraction of avocado + purified sterolic unsaponifiable fraction of soya | 58.21 | 4.43 | 90% | NS = 0 |

IN CONCLUSION

The mixture of purified total unsaponifiable of soya+total furanic unsaponifiable fraction of avocado stimulates aggrecan and TGFbeta1 (++) and inhibits IL-6 and NO (+++) and the aforementioned mixture has greater activity than the mixture of total furanic unsaponifiable fraction of avocado+ purified sterolic unsaponifiable fraction of soya, which does not stimulate aggrecan, or TGFbeta1, or inhibit IL-6, or NO.

Consequently, only the combination of the purified total unsaponifiable of soya according to the present invention mixed with the total unsaponifiable fraction of avocado, advantageously the furanic unsaponifiable, has a significant spectrum of activity on chondrocyte metabolism and is thus relevant to the treatment of osteoarthritis.

The invention claimed is:

1. A method for obtaining a purified total unsaponifiable of vegetable oil, comprising at least one step of entrainment of at least one vegetable oil refining industry by-product by carrier gas stripping with a temperature and vacuum gradient, to remove impurities initially present in said by-product, wherein the temperature and vacuum gradient is a temperature increasing from 80° C. to 250° C., and a progression of 0.5° C./min to 2° C./min, and a vacuum decreasing from 50 mbar to 1 mbar, and a progression of 0.1 mbar/min to 10 mbar/min.

2. The method of claim 1, wherein said vegetable oil refining industry by-product is a deodoriser distillate of vegetable oil and/or a physical refining condensate.

3. The method of claim 1, wherein the impurities are sapid and/or odorous compounds and/or chemical compounds resulting from the deterioration and the degradation of vegetable oils.

4. The method of claim 1, wherein said purified total unsaponifiable contains at most 1000 ppm of sapid and/or odorous compounds and/or chemical compounds resulting from the deterioration and the degradation of vegetable oils, compared to the total mass of the unsaponifiable.

5. The method of claim 1, wherein the purified total unsaponifiable is cleared of phytosanitary product residues.

6. The method of claim 1, wherein the vegetable oil is soya oil.

7. A method for obtaining a purified total unsaponifiable of vegetable oil from, comprising the following successive steps in the order shown:
(1) Saponifying at least one vegetable oil refining industry by-product in hydroalcoholic medium by a potash-type alkaline base,
(2) Liquid-liquid extraction by an organic solvent,
(3) Washing an organic extract from step (2) with water,
(4) Evaporating the organic solvent from the washed organic extract, and then
(5) Carrier gas stripping the washed organic extract under vacuum in order to obtain the purified total unsaponifiable of vegetable oil, wherein the said purified total unsaponifiable is cleared of the impurities initially present in the said by-product, and wherein the carrier gas stripping step (5) comprises at least one step (b) of entrainment with a temperature and vacuum gradient, at a temperature increasing from 80° C. to 250° C., and a progression of 0.5° C./min to 2° C./min, and under a vacuum decreasing from 50 mbar to 1 mbar, and a progression of 0.1 mbar/min to 10 mbar/min, to remove sapid and/or odorous compounds and/or chemical compounds resulting from the deterioration and the degradation of vegetable oils.

8. The method of claim 7, wherein saponifying step (1) is preceded by concentrating in unsaponifiable the vegetable oil refining industry by-product.

9. The method of claim 7, wherein the organic solvent of the liquid/liquid extraction (2) is selected from the group consisting of alkanes, chlorinated solvents such as 1,2-dichloroethane (DCE), fluorinated aromatic solvents, tert-butyl ethers, solvents comprising a silicon atom, MeTHF, and mixtures thereof.

10. The method of claim 7, wherein the carrier gas stripping step (5) comprises a preliminary step (a) of eliminating residual organic solvent.

11. The method of claim 7, wherein the carrier gas stripping step (5) further comprises a step (c) of elimination of phytosanitary product residues.

12. The method of claim 7, wherein the carrier gas in step (5) is dry steam or nitrogen.

13. The method of claim 7, wherein the vegetable oil is soya oil.

14. The method of claim 1, wherein the purified total unsaponifiable of vegetable oil contains at most 500 ppm of sapid and/or odorous compounds and/or chemical compounds resulting from the deterioration and the degradation of vegetable oils, compared to the total mass of the purified total unsaponifiable of vegetable oil.

15. The method of claim 1, wherein the purified total unsaponifiable of vegetable oil contains at most 100 ppm of sapid and/or odorous compounds and/or chemical compounds resulting from the deterioration and the degradation of vegetable oils, compared to the total mass of the purified total unsaponifiable of vegetable oil.

16. The method of claim 1, wherein said entrainment step is carried out at a temperature increasing from 145° C. to 210° C. and at a temperature progression of 0.5° C./min to 2° C./min.

17. The method of claim 1, wherein said entrainment step is carried out under a vacuum decreasing from 30 mbar to 2 mbar and a vacuum decreasing progression of 0.1 mbar/min to 10 mbar/min.

18. The method of claim 1, further comprising removing phytosanitary product residues from the purified total vegetable oil by at least one step of carrier gas stripping under vacuum, at a temperature between 180° C. and 250° C. and under a vacuum of 1 mbar to 5 mbar.

19. The method of claim 8, wherein said concentrating step is a molecular distillation.

20. The method of claim 7, wherein said washing (3) is carried out by liquid/liquid extraction.

21. The method of claim 7, wherein the carrier gas stripping step (5) comprises a preliminary step (a) of removing residual organic solvent carried out at a temperature between 80° C. and 145° C. and under a vacuum of 200 mbar to 30 mbar.

22. The method of claim 7, wherein said entrainment step (b) is carried out at a temperature increasing from 145° C. to 210° C. and a temperature progression of 0.5° C./min to 2° C./min.

23. The method of claim 7, wherein said entrainment step (b) is carried out under a vacuum decreasing from 20 mbar to 2 mbar and a vacuum decreasing progression of 0.1 mbar/min to 10 mbar/min.

24. The method of claim 7, wherein the carrier gas stripping step (5) further comprises a step (c) of removing phytosanitary product residues, at a temperature between 180° C. and 250° C. and under a vacuum of 1 mbar to 5 mbar.

25. The method of claim 7, wherein the carrier gas stripping step (5) further comprises a step (c) of removing phytosanitary product residues, at a temperature of 210° C. and under a vacuum of 2 mbar.

* * * * *